United States Patent [19]

Rentschler et al.

[11] Patent Number: 5,195,509
[45] Date of Patent: Mar. 23, 1993

[54] DISINFECTANT SYSTEM FOR A LITHOTRIPSY APPARATUS

[75] Inventors: Gunter Rentschler, Kraichtal-Münzesheim; Michael Burkhardt, Mühlacker, both of Fed. Rep. of Germany

[73] Assignee: Richard Wolf GmbH, Knittlingen, Fed. Rep. of Germany

[21] Appl. No.: 654,131

[22] Filed: Feb. 11, 1991

[30] Foreign Application Priority Data

Feb. 20, 1990 [DE] Fed. Rep. of Germany ....... 4005228

[51] Int. Cl.$^5$ ............................................. A61B 17/22
[52] U.S. Cl. ................................................. 128/24 EL
[58] Field of Search ................ 128/804, 660.03, 24 EL

[56] References Cited

U.S. PATENT DOCUMENTS

| | | | |
|---|---|---|---|
| 4,332,214 | 6/1982 | Cunningham | 119/19 X |
| 4,822,571 | 4/1989 | Nicholson et al. | 4/222 X |
| 5,046,483 | 9/1991 | Ogura | 128/24 EL |
| 5,060,634 | 10/1991 | Belikan et al. | 128/660.03 |

FOREIGN PATENT DOCUMENTS

| | | |
|---|---|---|
| 0265741 | 5/1988 | European Pat. Off. ........ 128/24 EL |
| 3220751 | 12/1983 | Fed. Rep. of Germany . |
| 3811316 | 10/1989 | Fed. Rep. of Germany . |
| 8703797 | 7/1987 | PCT Int'l Appl. . |
| 8912604 | 12/1989 | PCT Int'l Appl. . |

Primary Examiner—Ruth S. Smith
Attorney, Agent, or Firm—Panitch Schwarze Jacobs & Nadel

[57] ABSTRACT

There is disclosed lithotripsy apparatus comprising an ultrasonic shock wave generator having a coupling cushion which is adaptable to the body of a patient to be treated by means of the shock wave generator and which can be filled with water as the acoustic coupling medium between the body of the patient and the shock wave generator. Devices are provided for degasifying the water and for continuously disinfecting it for the prevention of slime formation therein, for example the growth of algae.

5 Claims, 1 Drawing Sheet

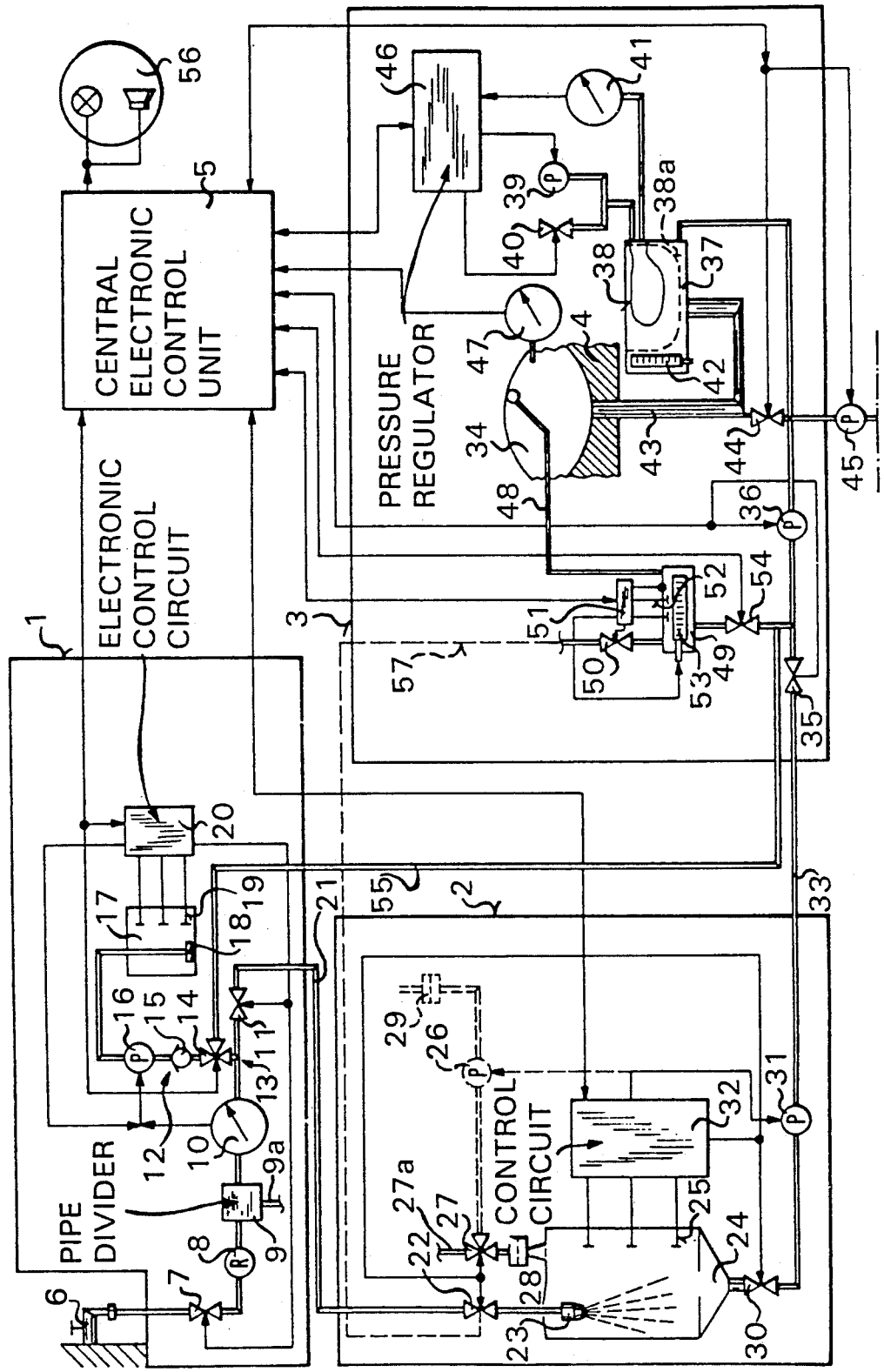

DISINFECTANT SYSTEM FOR A LITHOTRIPSY APPARATUS

FIELD OF THE INVENTION

The invention relates to lithotripsy apparatus comprising; an ultrasonic shock wave generator provided with a coupling cushion which is adaptable to the body of a patient to be treated by means of the shock wave generator, and which receives water as an acoustic coupling medium between the shock wave generator and the body of the patient; a device for controlling the pressure of the coupling medium in the coupling cushion; and a device for removing the gas from the coupling medium. Such apparatus are used for the destruction of concretions in a patient's body.

Water is commonly used as a coupling medium for introducing ultrasonic shock waves into the regions of a patient's body that are to be treated, since water has an acoustic impedance which is similar to that of the body tissue of a living being. The water should, however, be substantially free of gas and any gas produced during the shock wave therapy should be removed from the coupling medium. A coupling medium containing gas cannot be used efficiently in carrying out shock wave therapy because the acoustic impedance of said medium is thereby altered. Also, care must be taken to maintain constant, tight contact between patient's body and the coupling medium in such a way that the shock waves can always be precisely focused onto the concretion to be destroyed in the body.

BACKGROUND OF THE INVENTION

There is disclosed in DE-A-38 11 316, lithotripsy apparatus in which a sealed coupling cushion is filled with water as the coupling medium and is placed on a patient's body so that the shock wave energy can be transmitted through the medium of the water to a concretion to be disintegrated. A gas removal device ensures that the water in the water cushion is gas free and a controlled pressure regulating device ensures that the pressure in the water cushion is at an optimum value. The quality of the water used in the cushion can, however, deteriorate, for example algae may produce slime which reduces the efficiency of the shock wave transmission and thereby impairs the success of the treatment. A defect in the means for circulating the water for the water cushion, may allow water to escape into the open, so as to endanger the sterility of the room in which the patient is being treated. If an open coupling cushion is used the water may escape into the treatment room so that the treatment space or the treatment room must be cleaned and disinfected.

According to the disclosure of DE-A-35 44 628 and DE-A-32 20 751, the ultrasonic shock waves are coupled-in by way of a coupling bag or coupling cushion, filled with gas-free water, which is adapted to the body of the patient with the open part of the coupling bag or cushion contacting the patient or with a membrane shielding the patient. Such an enclosed water circuit has the disadvantage that the growth of algae or the like can cause the coupling medium rapidly to become fouled with slime. DE-A-35 44 628 and DE-A-32 20 751 do not, however, disclose how the water coupling medium is treated in order to prevent slime formation, and in the matter of degasification mention only that air removal tubes can be introduced in the region of the shock wave generator and the sealing edge.

With lithotripsy apparatus of the type under discussion, there is also difficulty in maintaining the contact pressure of the coupling cushion against the body of the patient at an optimum pressure when the weight of the patient's body acts against the coupling cushion. Since during positioning of the patient on the coupling cushion, the coupling medium exerts a counter pressure towards the patient, it may not be possible to bring a stone to be disintegrated into the focus of the shock waves.

EP-A-0 265 741 discloses apparatus for destroying concretions in the body of a living being. The apparatus comprises disintegrating shock wave generators, filled with a liquid coupling medium, and a liquid circuit with a container and circulating pump. The circulation of the liquid is in an operating circuit and a filling and gas removal circuit. In the filling and gas removal circuit, gas is removed from the liquid supplied with the aid of a vacuum pump and is subsequently fed from a storage container to the shock wave generator or generators.

This apparatus has the disadvantage that the use of containers for preparing the liquid and for removing gas from the liquid, entails that the apparatus is uneconomical of space. Further, since the coupling medium becomes fouled with slime it must be constantly replaced after only short periods of time.

Apart from the disadvantages just mentioned, particular care must be taken to ensure that no germs are transferred from patient to patient by way of the coupling medium, especially if the coupling cushion is exposed towards the patient.

SUMMARY OF THE INVENTION

The invention is intended to provide lithotripsy apparatus that is economical of space and is of simple construction, the quality of the coupling medium being safeguarded, and water from a mains drinking water supply being usable as the coupling medium.

According to the present invention lithotripsy apparatus comprises; a shock wave generator provided with a coupling cushion, adaptable to the body of a patient to be treated and which receives water as an acoustic coupling medium between the shock wave generator and the body of the patient; a device for controlling the pressure of the water in the coupling cushion; a device for removing the gas from the coupling medium; and before the degasifying device, a disinfecting device in which are a storage container for receiving a disinfectant, a control circuit for the storage container and a metering device connected to the storage container for supplying disinfectant to the coupling medium.

The quality of the coupling medium which may be taken directly from a main drinking water supply, remains unimpaired or may even be improved, as the coupling medium is disinfected so that germs cannot multiply, or algae grow in the coupling medium. The coupling medium is accordingly prevented from becoming fouled by slime, thereby ensuring that the quality of transmission of the ultrasonic shock wave energy to the body of the patient is guaranteed and that said energy has a high degree of effectiveness. Similarly, when an open coupling cushion is used or if there is a defect in the lithotripsy apparatus, the germ-free atmosphere of the treatment room or treatment space is not impaired, so that it does not need to be disinfected. The provision of the disinfecting device adds little to the space needed to accommodate the lithotripsy apparatus.

The metering device may comprise a metering pump, a nonreturn valve following the pump, and a magnetic valve for introducing the metered disinfectant into the coupling medium.

The coupling cushion may communicate with a pressure equalising vessel defining a space a part of which is filled with gas and which is separated by a flexible membrane from the remainder of the space which can be filled with coupling medium.

When smaller quantities of disinfectant are used the metering pump of the disinfecting device should be intermittently operated. Furthermore, in order to achieve a long period of usefulness of the prepared coupling medium, a pipe may be provided which links a main circuit for filling and emptying the coupling cushion to the disinfecting device.

BRIEF DESCRIPTION OF THE DRAWING

The single FIGURE is a block schematic diagram of a lithotripsy apparatus.

DETAILED DESCRIPTION OF THE INVENTION

A lithotripsy apparatus according to an embodiment of the invention comprises a disinfecting device 1, a water degasifying device 2 operating according to the vacuum gas removal principle, a main circuit 3 for filling and emptying a water containing. closed coupling cushion 34, of a shock wave generator 4, and a central electronic control unit 5 for controlling the devices 1 and 2 and the main circuit 3.

The disinfecting device 1 serves to prevent the growth and proliferation of bacteria. viruses, fungi, algae and the like, thereby to prevent the water in the coupling cushion 34 from becoming fouled with slime and to prevent possible contamination of a patient under the treatment. The device 1 is preferably connected to the main drinking water supply via a water tap 6. The connection of the device 1 to the water supply is made by way of a first magnetic valve 7 which is connected in series with a water flow regulator 8, a pipe divider 9, a flow volume measuring device 10 and a second magnetic valve 11. A metering device 12 is connected to the pipe connecting the magnetic valve 11 to the flow volume measuring device 10. The metering device 12, as seen from a disinfectant injection point 13, comprises, connected in series, a third magnetic valve 14, a nonreturn valve 15, a metering pump 16 and a disinfectant storage container 17 provided with a suction pipe 18 and disinfectant level sensors 19. The disinfecting device 1 is controlled by means of an electronic control circuit 20.

The disinfecting device 1 is connected by way of a feed pipe 21, which is, in turn, connected to the outlet of the second magnetic valve 11, to the water degasifying device 2. The pipe 21 is connected to the device 2 by way of a magnetic valve 22, for supplying water to an injection nozzle 23 terminating within a gas removal container 24 having water level sensors 25. A vacuum pump 26 is connected to the container 24 by way of a magnetic valve 27 and a water-impermeable filter 28 communicating with the interior of the gas removal container 24. The vacuum pump 26 is connected in series with a filter 29 for releasing suctioned-off gas into the atmosphere. The outlet of the container 24 is connected to a magnetic valve 30 which is, in turn, connected in series with a pump 31, the use of which is described below, with regard to another embodiment of the water degasifying device 2. The degasifying device 2 is controlled by means of a control circuit 32.

The outlet side of the pump 31 is connected by way of a feed pipe 33, to the main circuit 3 for filling and emptying the coupling cushion 34 of the shock wave generator 4. The pipe 33 is connected to a magnetic valve 35, which is in turn connected to the inlet side of a circulating pump 36 the outlet side of which is connected to a pressure equalising container 37. The container 37 is provided with a laterally inserted balloon 38 which is supplied with compressed air by means of an air pump 39 and is emptied with the aid of a magnetic valve 40. A limit indicator 41 is arranged to monitor the pressure relationships in the balloon 38. Instead of the balloon 38, a membrane 38a may be used for dividing the container 37 so as to provide a sub-chamber, which can be filled with compressed air. The pressure equalising chamber 37 may be provided with a heater 42. The water containing part of the equalising container 37 is connected to the water chamber of the coupling cushion 34 by way of a connecting pipe 43 of relatively large cross-section. At its lowest point, the pipe 43 is provided with a magnetic valve 44 for use in emptying the system by means of a suction pump 45. The pressure in the coupling cushion 34 is controlled by means of a pressure regulator 46.

The water level in the water chamber of the coupling cushion 34 is monitored by means of a pressure gauge 47. There leads from the region of the highest point of the coupling cushion 34, a suction pipe 48 connected to a container 49. The container 49 is arranged to be ventilated by means of a valve 50 regulated by means of a control device 51. The water level in the container 49 is controlled by means of level sensors 52. Within the container 49 is a heater 53 for heating the contents thereof. The base of the container 49 is connected by way of a magnetic valve 54 to the pipe connecting the magnetic valve 35 to the circulating pump 36. Between the valve 54 and said connecting pipe there is connected a pipe 55 which is in turn, connected to said third magnetic valve 14 of the disinfecting device 1.

The apparatus described above operates as follows:

The disinfecting device 1 connected to the main drinking water supply is filled by opening the magnetic valves 7 and 11, whereby a substantially constant stream of water is caused to flow through the flow regulator 8, the pipe divider 9 and the flow volume measuring device 10, and by way of the magnetic valve 11, into the feed pipe 21 of the water degasifying device 2. Disinfectant from the storage container 17 is thus added to the water by the metering pump 16 at the disinfectant injection point 13. The metering pump 16 is controlled by the flow volume measuring device 10 and the control circuit 20, so as to ensure that the disinfectant is always metered in accordance with the actual volume of water flowing. independently of the pressure of the mains supply. Where there is a very strong concentration of the disinfectant in the storage container 17, the metering pump 16 is only controlled intermittently by the volume measuring device 10. During the intervals of such control the nonreturn valve 15 ensures that the supply of disinfectant from the storage container 17 is blocked.

The disinfectant level sensor 19 monitors the disinfectant level in the storage container 17 and passes information as to said level to the control circuit 20. The circuit 20 ensures that when the storage container 17 is empty, the metering pump 16 cannot be put into operation by the flow volume measuring device 10, and also ensures that the magnetic valves 7 and 11 are closed. The circuit 20 further ensures that at the start of the operation when the storage container 17 is already empty, the magnetic valves 7 and 11 are not opened in the first place. The control circuit 20 reports the empty condition of the container 17 to the central control unit 5 which signals such condition by activating an optical and/or acoustic indicator 56 arranged for example on the operating panel of the lithotripsy apparatus.

The magnetic valve 11 also ensures that any vacuum there may be in the pipe 21 does not cause the storage container 17 to be sucked dry by the next system. If the pressure on the inlet side of the valve 11 falls below a predetermined minimum level, the pipe divider 9 isolates the disinfecting device 1 from the drinking water supply by means of drain 9a in order to prevent disinfectant from getting into the drinking water.

The water is supplied to the water degasifying device 2 by way of the pipe 21. The gas removal container 24 is evacuated by the vacuum pump 26 to a desired pressure which is dependent upon the water temperature. Said desired pressure may be adjusted with the aid of pressure pick-up means or the pumping time of the pump 26 may be selected in accordance with the output of the vacuum pump 26. When said desired pressure has been reached, the magnetic valve 22 is opened, to allow the water to pass from the disinfecting device 1. The water under pressure in the device 1, assisted by the vacuum in the gas removal container 24, is thus forced and sucked through the injection nozzle 23 into the container 24. As the water droplets enter the container 24, gas bubbles are separated from the water by cavitation. The gas so produced is then sucked by the pump 26 through the water impermeable filter 28 and the valve 27 and is expelled into the atmosphere by way of the filter 29. When the water level in the gas removal container 24 has reached the required value as measured by the water level sensors 25, the control circuit 32 closes the magnetic valve 22 so as to terminate the filling of the container 24.

The vacuum in the gas removal container 24 is maintained for some time after said termination of the filling of the container 24, so that gas bubbles carried along by the water as a result of the high injection rate thereof, so as to be mixed in with the water, rise to the surface of the water and are suctioned off and expelled into the atmosphere in the manner described above. The fully degasified water now contained in the gas removal container 24, after the ventilation thereof by way of the valve 27 and the water impermeable filter 28, is then supplied by way of the magnetic valve 30 to the main circuit 3 for filling the coupling cushion 34 of the shock wave generator 4. Further water can subsequently be supplied to the main circuit 3 in the manner described above. Such degasifying and filling cycle is continued until the cushion 34 has been filled with the necessary volume of degasified and disinfected water.

According to said other embodiment of the degasifying device 2, the vacuum pump 26, which is expensive, is omitted and the pump 31, which is for example a gear pump, which can produce sufficient suction on its suction side, is provided as aforesaid between the magnetic valve 30 of the degasifying device 2 and the feed pipe 33 to the coupling cushion 34. In this embodiment the gas removal container 24, which has not been evacuated through the magnetic valve 22 operated by the control circuit 32, is first filled with a given volume of water from the disinfecting device 1. The water level in the container 24 is as in the first embodiment of the device 2 controlled by the control circuit 32 by way of the water level sensors 25 and the magnetic valve 22. When the selected water level has been reached, the control circuit 32 shuts the magnetic valve 22, opens the magnetic valve 30 and activates the pump 31. The consequent suctioning off a proportion of the water in the gas removal container 24 causes a vacuum to be formed in the space between magnetic valve 22 and the surface of the water in the container 24. When the said desired pressure in the gas removal container 24 has been reached, as determined by the water level sensors 25, and has been reported to the control circuit 32, the control circuit 32 causes the magnetic valve 22 to open. The water then entering by way of the injection nozzle 23 is degasified according to the principle described above and the gas bubbles can if required be released to the atmosphere through vent 27a by way of the water-impermeable filter 28 and the magnetic valve 27. Thus, in contrast with the degasifying process using the vacuum pump 26 according to the first embodiment of the device 2, a continuous gas removal and filling cycle can be achieved.

The water degasified in the manner just described is degasified to almost the same extent as in said first embodiment, despite the fact that it consists of a mixture of the degasified water and the gasified water initially introduced into the container 24. Total degasification is achieved, because the volume of gasified water in relation to the volume of water that is required for filling the coupling cushion 34, and, therefore, in relation to the volume of degasified water, is very small.

The degasified water is supplied to the main circuit 3 by way of the pipe 33. When the magnetic valve 30 is open and the pump 31 is switched on, the water pumped to the main circuit 3 by way of the pipe 33, after the valve 35 has been opened and the circulating pump 36 has been switched on, is pumped by the pump 36 through the pressure equalising container 37 into the coupling cushion 34 until the latter as been completely filled with degasified water. During this filling process, the free space for the through-flowing water in the pressure equalising container 37 is kept to a minimum. To this end, the balloon 38 is inflated by the pump 39 until it takes up almost the entire volume of the container 37, since it is the cushion 34 that is to be filled with water and not the equalising container 37. The coupling cushion 34 is accordingly disposed to allow a maximum of water to be taken up.

Before the cushion 34 is filled with water, the air in the cushion 34 and in its connecting pipe 43, is fed to the container 49 via the suction pipe 48. Since the pipe 43 is of large cross-section control variations resulting from the detection of delayed pressure variations can be kept to a minimum. The container 49 can be ventilated through the valve 50 which is operated by the control device 51. The valve 50 remains open until the container 49 and thus also the coupling cushion 34 are completely filled with water. The extent to which the container 49 has been filled is determined with the aid of the level sensors 52 and the valve 50 is operated by the control device 51.

The extent to which the coupling cushion 34 has been filled is monitored by the pressure gauge 47 which upon detecting a predetermined pressure, signals the central control unit 5 which, in turn, emits appropriate control signals which put the disinfecting device 1 and the degasifying device 2 out of operation, shut the magnetic valve 35 and open the magnetic valve 54. The circulating pump 36 now circulates the water in a closed circuit. The heater 42 heats the water for example to body temperature. The heater 42 is controlled by the control device 51, since the heater 42 must only be operated when it is immersed. Since the heater 42 is in the vessel 37, and is not in the container 49, the container 49 can be very small. The control device 51 and the level sensors 52 may be omitted and the valve 50 may, for example, be replaced by a simple float switch.

The water displaced by a patient when being positioned for treatment is taken up by the equalising container 37 and the pressure in the system is maintained constant by the pressure regulator 46 with the aid of the magnetic valve 40 of the air pump 39 and the limit indicator 41. The limit indicator 41 ensures that the balloon 38 is not overinflated so as to cause itself and the pressure equalising container 37 to be damaged or to burst.

When the shock wave generator 4 is being used, the prepared water is circulated by the circulating pump 36 in a closed circuit after the magnetic valve 35 has been closed, the circulating water being kept at the desired temperature by the heater 42 or 53.

In order to keep the prepared water in the lithotripsy apparatus as long as possible, the central control unit 5 controls, if necessary, the disinfecting device 1 in such a way that disinfectant reaches the disinfectant injection point 13 of the closed water circuit by way of the magnetic valve 14 and the pipe 55.

Any gas bubbles produced during the operation of the lithotripsy apparatus, for example, as a result of cavitation during shock wave therapy or as a result of gas given off by the disinfection agent, are removed from the coupling cushion 34 through the suction tube 48 and by way of the container 49 and the valve 50 and the gas is released into the atmosphere in the same way as the air is removed during the filling process.

The coupling cushion 34 may be emptied at anytime by way of the magnetic valve 44 and the suction pump 45 and emptying of the apparatus can likewise be effected by way of the central control unit 5. The other containers may be emptied by equivalent means.

If large volumes of air and/or water are to be suctioned off from the coupling cushion 34, as may be necessary when changing its membrane, the main circuit 3 may be modified by omitting the container 49, the device 51, the sensors 52, and the heater 53. In this case the valve 50 is replaced by a valve (not shown) having an inlet and two outlets and being connected by way of a pipe 57 (shown in broken lines) to the magnetic valve 22 of the degasifying device 2. Suction then takes place by way of the pipe 48 directly to said replacement valve and further by way of the pipe 57 to the valve 22. In this case the said replacement valve and the valve 54 are connected to each other by one pipe only.

Instead of the closed coupling cushion 34 an open coupling cushion (not shown) may be used.

By appropriate choice of disinfectant, for example, a disinfectant of which less than 0.5 ppm needs to be added to the water, the storage container 17 of the disinfecting device 1 can be very small whilst still being capable of containing enough disinfectant to last throughout a whole service interval.

What is claimed is:

1. A lithotripsy apparatus comprising:
an ultrasonic shock wave generator;
a coupling cushion for receiving water which acts as an acoustic coupling medium between the shock wave generator and a body of a patient to be treated by said apparatus, the coupling cushion being adaptable to the patient's body;
a pressure device connected to the coupling cushion for controlling the pressure of the coupling medium therein;
a degasifying device connected to the coupling cushion for degasifying the coupling medium; and
a disinfecting device connected to the degasifying device and having a storage container for receiving a disinfectant, a control circuit for controlling material flow of the disinfectant from the storage container and a metering device connected to the storage container for introducing disinfectant into the coupling medium.

2. Apparatus as claimed in claim 1, wherein the metering device further comprises a disinfectant metering pump, a magnetic valve for introducing the disinfectant metered into the coupling medium to be supplied to the coupling cushion, and a nonreturn valve connected between said metering pump and said magnetic valve.

3. Apparatus as claimed in claim 2, wherein said disinfecting device further comprises a volume measuring device which cooperates with the control circuit for intermittently controlling the operation of said metering pump.

4. Apparatus as claimed in claim 1, further comprising means or filling and emptying the coupling cushion and a pipe for connecting the disinfecting device for the filling and emptying means.

5. Apparatus as claimed in claim 1, wherein the pressure device comprises a pressure equalizing container for communicating with the coupling cushion and which defines a first gas filled space and a second space for receiving the coupling medium, said pressure equalizing container including a flexible membrane for separating said spaces, wherein the amount of disinfectant added to the coupling medium is based on the amount of water received by the coupling cushion.

* * * * *